US00PP36342P2

(12) United States Plant Patent
Merritt

(10) Patent No.: US PP36,342 P2
(45) Date of Patent: Dec. 31, 2024

(54) PEAR TREE NAMED 'Rosebutter'

(50) Latin Name: *Pyrus communis*
Varietal Denomination: Rosebutter

(71) Applicant: Rose Merritt, Bow, WA (US)

(72) Inventor: Rose Merritt, Bow, WA (US)

( * ) Notice: Subject to any disclaimer, the term of this patent is extended or adjusted under 35 U.S.C. 154(b) by 0 days.

(21) Appl. No.: 18/545,574

(22) Filed: Dec. 26, 2023

(51) Int. Cl.
*A01H 5/08* (2018.01)
*A01H 6/74* (2018.01)

(52) U.S. Cl.
USPC ..... Plt./176

(58) Field of Classification Search
USPC ..... Plt./176
See application file for complete search history.

*Primary Examiner* — Karen M Redden
*Assistant Examiner* — Zachariah Allan Kay
(74) *Attorney, Agent, or Firm* — Michelle Bos Legal LLC

(57) ABSTRACT

A new European-type pear tree named 'Rosebutter' notable for its fruit, which exhibits smooth russeted skin, juicy melting flesh and well-balanced flavor.

5 Drawing Sheets

Latin name: *Pyrus communis.*
Variety denomination: Rosebutter.

BACKGROUND OF THE VARIETY

'Rosebutter' is a new and distinct European pear tree, originating as a chance seedling discovered in 2011 in a cultivated orchard of pear trees of assorted varieties located in Bow, Washington. 'Rosebutter' was first asexually propagated by grafting at Bow, Washington in 2012. The variety has been observed to remain true to type over successive asexually propagated generations.

BRIEF DESCRIPTION OF THE VARIETY

'Rosebutter' was first selected for its fruit, which exhibits smooth russeted skin, juicy melting flesh and well-balanced flavor.

Fruit of 'Rosebutter' is ready for harvest about one month earlier than similar variety 'Comice' pear (not patented). 'Rosebutter' is further distinguished from 'Comice' as shown in Table 1 below.

TABLE 1

Comparison of 'Rosebutter' to 'Comice'

| | 'Rosebutter' | 'Comice' |
|---|---|---|
| Bruising | Less susceptible to bruising | Very delicate skin bruises easily |
| Skin color | Yellow green with fine russet covering surface | Yellow green with a blush |
| Harvest yield | Heavy yield | Moderate yield |
| Harvest date | Mid- to late September | Mid- to late October |

BRIEF DESCRIPTION OF THE PHOTOGRAPHS

The attached photographs were taken during the 2023 growing season near Wapato, Washington. The tree shown in the photograph was planted in 2021.

DETAILED BOTANICAL DESCRIPTION OF THE VARIETY

Figure 1:
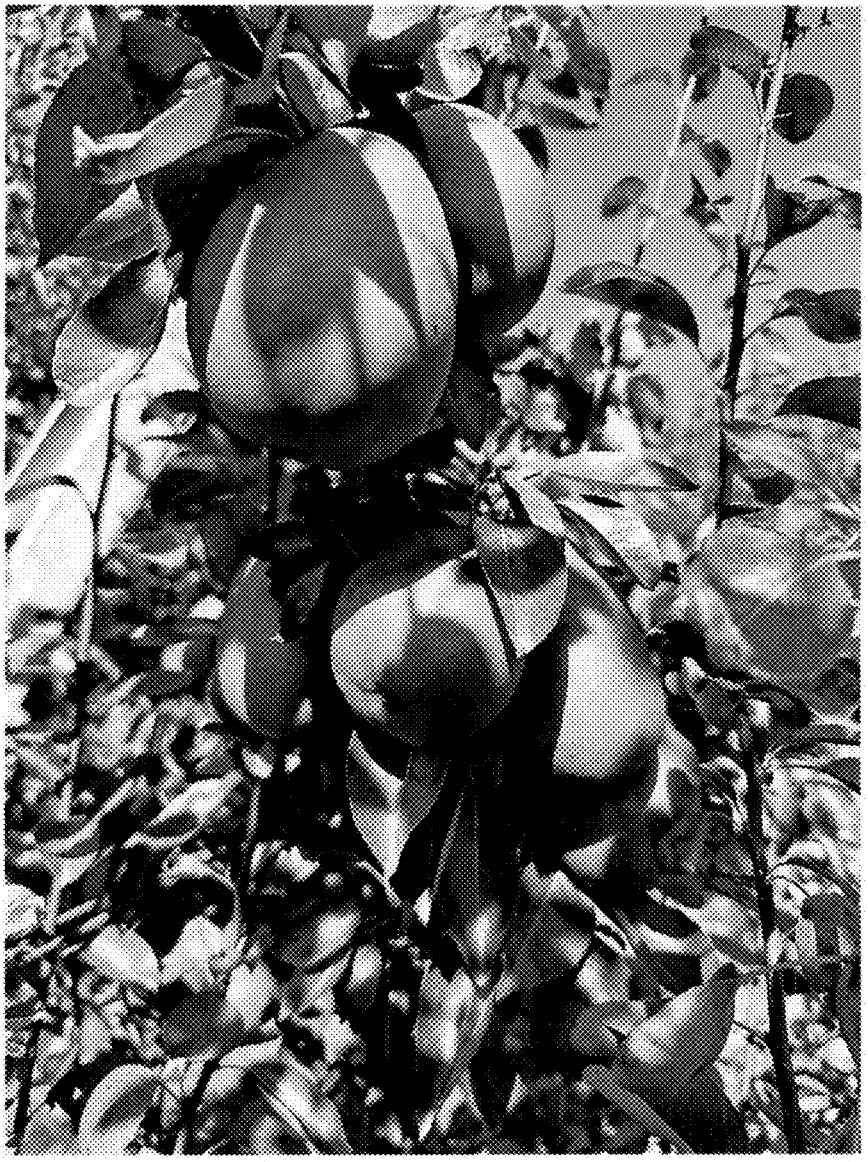
FIG. 1 shows fruits, leaves and branches on a 'Rosebutter' pear tree.
Figure 2:
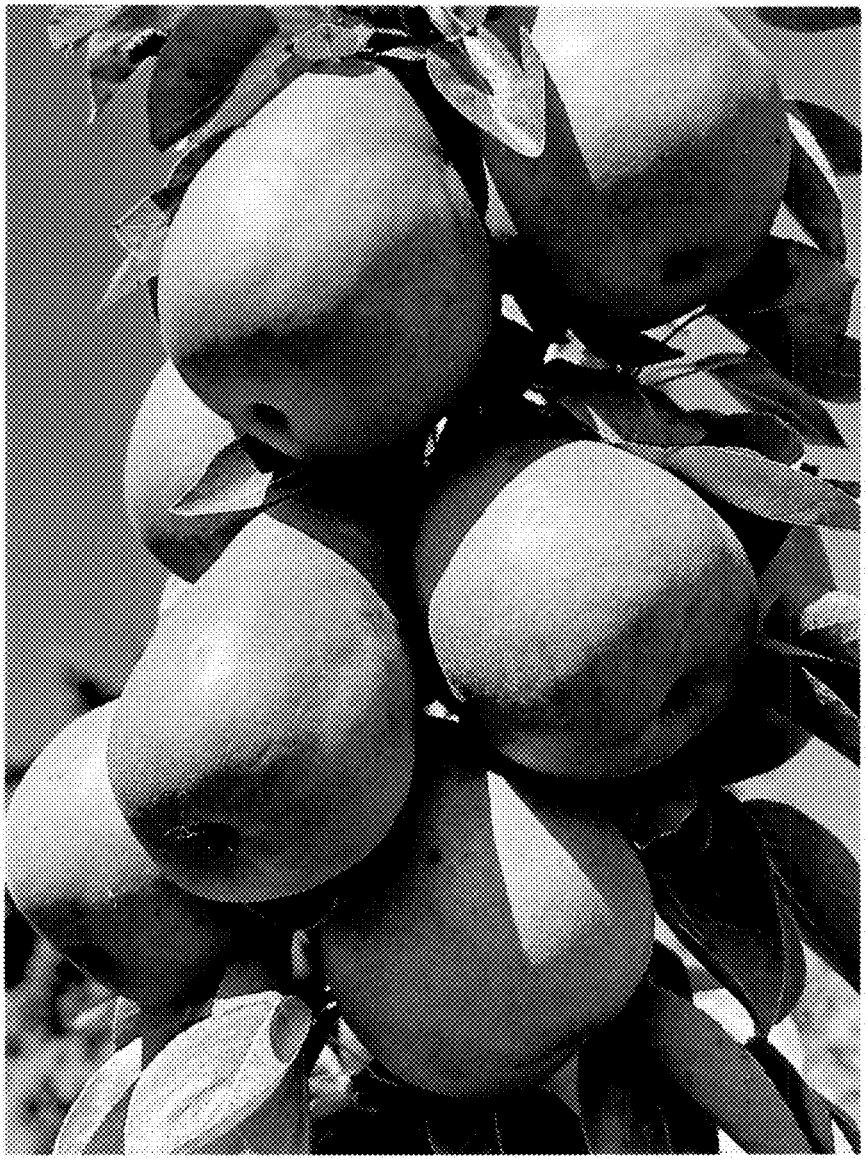
FIG. 2 shows fruits and leaves on a 'Rosebutter' pear tree.
Figure 3:
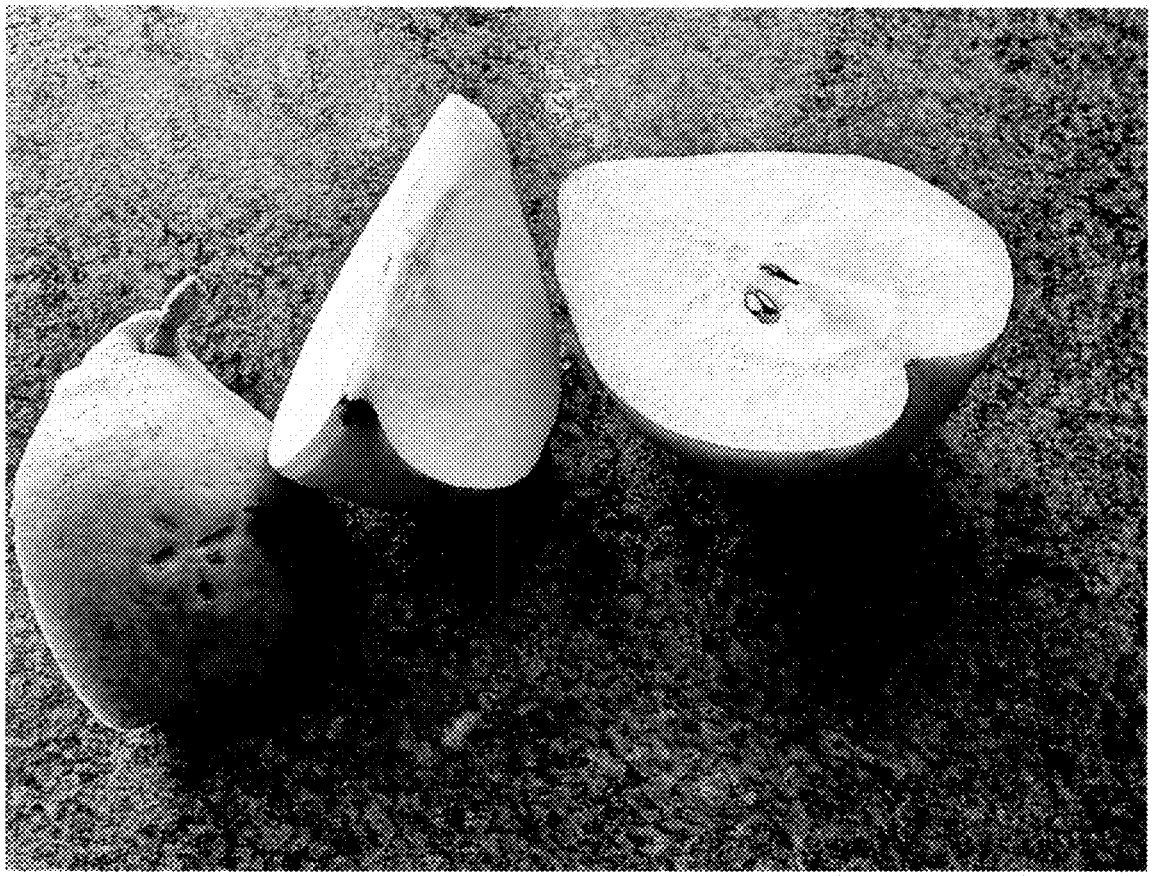
FIG. 3 shows section 'Rosebutter' pears.
Figure 4:
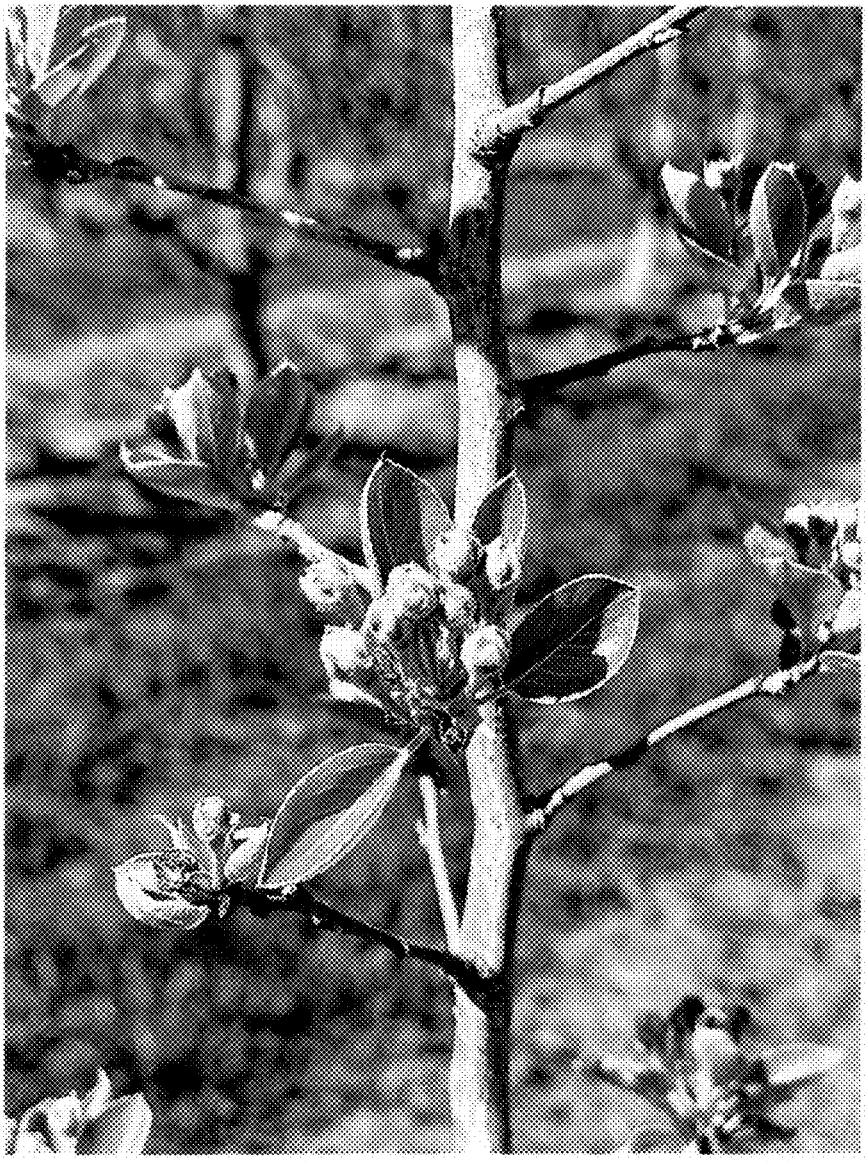
FIG. 4 shows the trunk and flower buds on a young 'Rosebutter' pear tree; and, FIG. 5 shows fully opened blossoms on a 'Rosebutter' pear tree.
Figure 5:
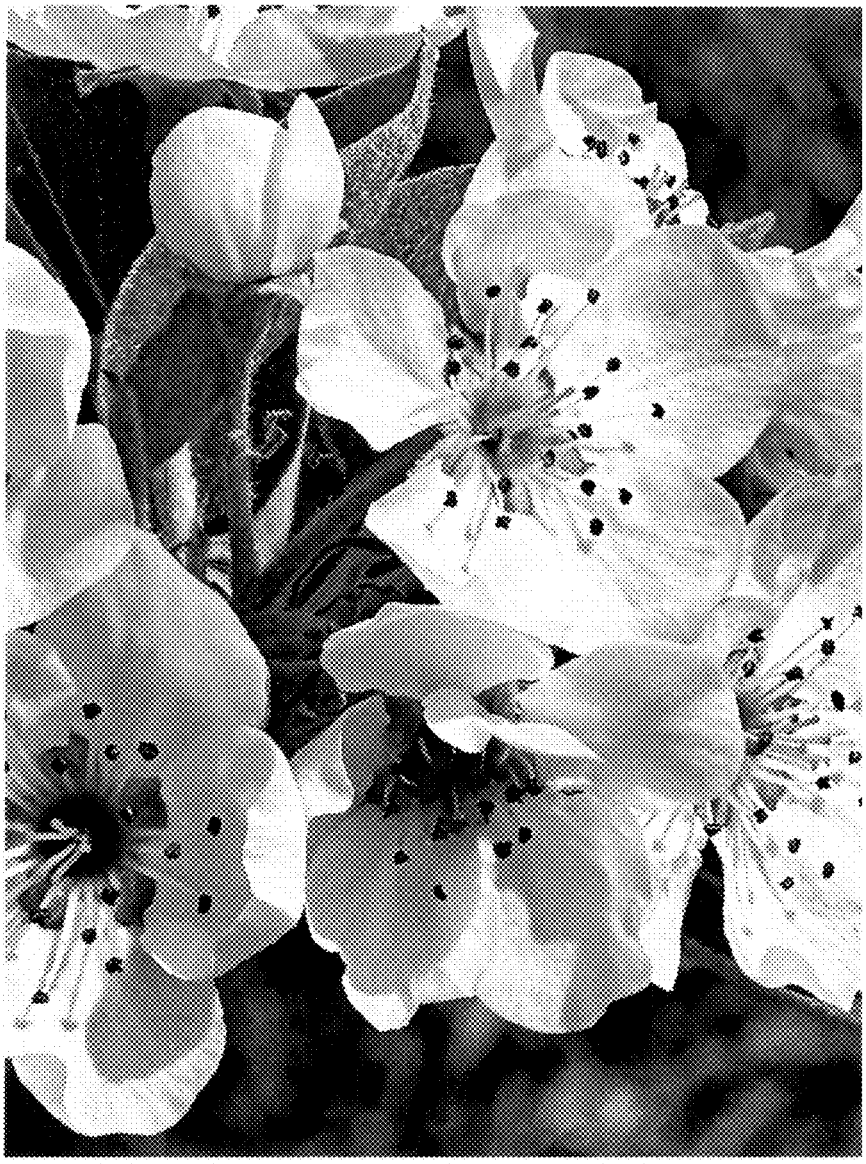

The following detailed botanical description is based on observations made during the 2023 growing season at Wapato, Washington of two-year-old 'Rosebutter' trees grown on 'Old Home x Farmingdale 97' rootstock (not patented). Colors descriptions are made with reference to The R.H.S. Colour Chart, $4^{th}$ ed. (Royal Horticultural Society, 2001). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Medium, similar to 'Comice'.
*Type.*—Ramified.
*Habit.*—Upright.
*Height.*—2.1 m.
*Spread.*—0.6 m.
*Trunk diameter at* 30 *cm above the graft.*—2.5 cm.
*Bark texture.*—Rough.
*Bark color.*—Greyed-orange 173A.
*Lenticel length.*—4 mm.
*Lenticel width.*—1 mm.
*Lenticel shape.*—Elongated.
*Lenticel color.*—White 155B.
*Lenticel density per* 10 $cm^2$.—9.

Branch (fruiting branches located at around 1 m above the graft union):
*Length.*—54 cm.
*Diameter.*—0.6 cm.
*Crotch angle.*—70 degrees.
*Bark color.*—Greyed-orange 173A.
*Lenticel length.*—1 mm.
*Lenticel width.*—1 mm.
*Lenticel shape.*—Circular.
*Lenticel color.*—Yellow-green 153A.
*Lenticel density per cm$^2$.*—About 15.
One year old shoot:
*Length.*—26 cm.
*Diameter.*—0.4 cm.
*Color.*—Greyed-orange 175B.
*Pubescence.*—None.
*Internode length.*—3.5 cm.
*Lenticel length.*—0.5 mm.
*Lenticel width.*—0.5 mm.
*Lenticel shape.*—Circular.
*Lenticel color.*—Yellow-green 153A.
*Lenticel density per cm$^2$.*—About 24.
*Vegetative bud shape.*—Elongated.
Leaves:
*Shape.*—Ovate.
*Length.*—5.5 cm.
*Width.*—3.5 cm.
*Blade margin.*—Serrate.
*Apex shape.*—Acute.
*Base shape.*—Rounded.
*Color of upper surface.*—Green 137C.
*Color of lower surface.*—Green 138D.
*Attitude in relation to shoot.*—Upward.
Petiole:
*Length.*—2.5 cm.
*Diameter.*—0.5 mm.
*Color.*—Yellow-green 154B.
*Stipules.*—Present on distal end of branch only.
*Stipule color.*—Green 137C.
*Stipule length.*—1 cm.
*Stipule width.*—0.2 cm.
*Stipule shape.*—Elliptic.
*Stipule apex.*—Acute.
Fruit:
*Quantity per cluster.*—2 to 3 after thinning.
*Height.*—8.8 cm.
*Diameter.*—6.8 cm.
*Weight.*—Average 220 g.
*Position of maximum diameter.*—Equator.
*Symmetry in longitudinal section.*—Asymmetrical.
*Profile of sides.*—Convex.
*Skin texture.*—Smooth.
*Background color of skin.*—Yellow-green 153B.
*Over color of skin.*—Yellow-green 152B russet over >90% of surface.
*Lenticels.*—Dense, circular shape.
*Length of stalk.*—1.5 cm.
*Diameter of stalk.*—0.5 cm.
*Curvature of stalk.*—Somewhat curved.
*Attitude of stalk in relation to axis of fruit.*—Angled.
*Stalk color.*—Grey-brown 199B.
*Depth of eye basin.*—5 mm.
*Width of eye basin.*—2 cm.
*Attitude of sepals at harvest.*—Erect.
*Firmness of flesh.*—Medium.
*Flesh texture.*—Crisp, melting.
*Aroma.*—Mild.
*Flavor.*—Sweet, notes of hazelnut.
*Juiciness.*—Juicy.
*Brix.*—10° Brix (4 weeks post-harvest).
*Flesh color.*—Green-white 157C.
Seeds:
*Quantity per fruit.*—7.
*Shape.*—Oval with pointed ends.
*Length.*—10 mm.
*Width.*—5 mm.
*Color.*—Brown 200B.
Harvest:
*Harvest date.*—Sep. 21, 2023.
*Number of picks.*—1.
*Pests and diseases.*—No resistance or susceptibility noted to date.
*Harvest yield.*—Very productive, heavy yield.
*Storage.*—Approximately 90 to 120 days at 31° F. in standard cold storage.
Winter hardiness: Hardy in area tested, USDA Hardiness Zone 7a (average annual low temperature 0° to 5° F.).
Market use: Fresh.

The invention claimed is:

1. A new and distinct pear tree named 'Rosebutter' substantially as illustrated and described herein.

* * * * *